(12) United States Patent
Mishima et al.

(10) Patent No.: US 6,383,170 B1
(45) Date of Patent: May 7, 2002

(54) DISPOSABLE DIAPER

(75) Inventors: Yoshitaka Mishima; Toshifumi Otsubo, both of Kagawa-ken (JP)

(73) Assignee: Uni-Charm Corporation (JP)

( * ) Notice: Subject to any disclaimer, the term of this patent is extended or adjusted under 35 U.S.C. 154(b) by 0 days.

(21) Appl. No.: 09/574,920

(22) Filed: May 19, 2000

(30) Foreign Application Priority Data

May 21, 1999 (JP) .............................. 11-142335

(51) Int. Cl.[7] .................................................. A61F 13/15
(52) U.S. Cl. ............................ 604/385.19; 604/385.24; 604/385.27; 604/385.28
(58) Field of Search .................. 604/385.19, 385.24, 604/385.27, 385.28

(56) References Cited

U.S. PATENT DOCUMENTS

| 4,662,877 A | * | 5/1987 | Williams ..................... 604/385 |
| 5,304,160 A | | 4/1994 | Igaue et al. |
| 5,672,166 A | * | 9/1997 | Vandemoortele ......... 604/385.2 |
| 5,904,674 A | | 5/1999 | Bonjour |
| 6,110,158 A | * | 8/2000 | Kielpikowski ......... 604/385.28 |
| 6,186,996 B1 | * | 2/2001 | Martin ................... 604/385.19 |
| 6,245,583 B1 | * | 7/2001 | Coates ................... 604/385.14 |

FOREIGN PATENT DOCUMENTS

| JP | A-5-305109 | 11/1993 |
| JP | A-8-322878 | 12/1996 |
| WO | WO 98/53779 | 12/1998 |

* cited by examiner

Primary Examiner—John G. Weiss
Assistant Examiner—Michael Bogart
(74) Attorney, Agent, or Firm—Baker & Daniels

(57) ABSTRACT

A disposable diaper including a pair of elasticized gasket cuffs disposed in transversely opposite sides of the diaper, a pair of elasticized barrier cuffs disposed adjacent the gasket cuffs and a three-dimensional feces receiving section extending at least partially across a crotch region of the diaper. The feces receiving section is defined by a pair of elasticized first barrier flaps transversely opposite to and spaced from each other and a pair of elasticized second barrier flaps longitudinally opposed to and spaced each other and extending transversely between the first barrier flaps.

3 Claims, 5 Drawing Sheets

DISPOSABLE DIAPER

BACKGROUND OF THE INVENTION

This invention relates to a disposable diaper for absorption and containment of excretion, and more particularly, to a disposable diaper having a three-dimensional section for receiving feces.

Japanese Patent Application Disclosure No. 1993-305109 describes a disposable diaper in which a topsheet intended to come in contact with the wearer's skin is formed in its central zone with an opening shaped to be relatively long as viewed in its longitudinal direction. The opening is provided along its peripheral edge with an elastic element adapted to be elastic in the longitudinal direction.

Japanese Patent Application Disclosure No. 1996-322878 describes a disposable diaper in which a liquid-absorbent core is divided in a crotch region in longitudinally front and rear sections spaced from each other by a desired distance. In the space left between these two sections, a topsheet and a backsheet are jointed to each other and a pair of flaps extend transversely to cover the space.

The diaper described in the Japanese Patent Application Disclosure No. 1993-305109 intends to ensure that excretion discharged on the diaper reliably flows into the opening. However, such intention can not necessarily be achieved when the excretion is in the form of loose passage because, even if discharged onto the crotch region or the rear waist region of the diaper, such loose passage may spread over the topsheet into the front waist region and soil the urinogenital organs.

The diaper described in the Japanese Patent Application Disclosure No. 1996-322878 intends to prevent loose passage from flowing into the front waist region. However, it is impossible for this known diaper to confine such loose passage in the vicinity of the spot onto which the loose passage has been discharged. As a result, the loose passage may spread over the topsheet in the crotch and rear waist regions.

SUMMARY OF THE INVENTION

An object of this invention is provide a disposable diaper that is designed so that body wastes discharged thereon is reliably prevented not only from flowing into the front waist region but also from flowing and/or spreading in the crotch and rear waist regions.

According to this invention, there is provided a disposable diaper having a front waist region, a rear waist region and a crotch region therebetween, the diaper comprising: a liquid-permeable topsheet, a liquid-impermeable backsheet and a liquid-absorbent core therebetween; a pair of elasticized gasket cuffs longitudinally extending outward from transversely opposite side edges of the core; a pair of elasticized barrier cuffs longitudinally extending adjacent the gasket cuffs on an upper surface of the diaper; and a feces receiving section extending at least partially across the crotch and the rear waist regions between the barrier cuffs, wherein the feces receiving section is defined by a pair of elasticized first barrier flaps transversely opposed to and spaced from each other and extending longitudinally of the diaper and a pair of elasticized second barrier flaps longitudinally opposed to and spaced each other and extending transversely between the first barrier flaps and connecting to the first barrier flaps.

DETAILED DESCRIPTION OF THE PREFERRED EMBODIMENTS

A disposable diaper according to this invention will be described in more details by way of example with reference to the accompanying drawings.

Figure 1:
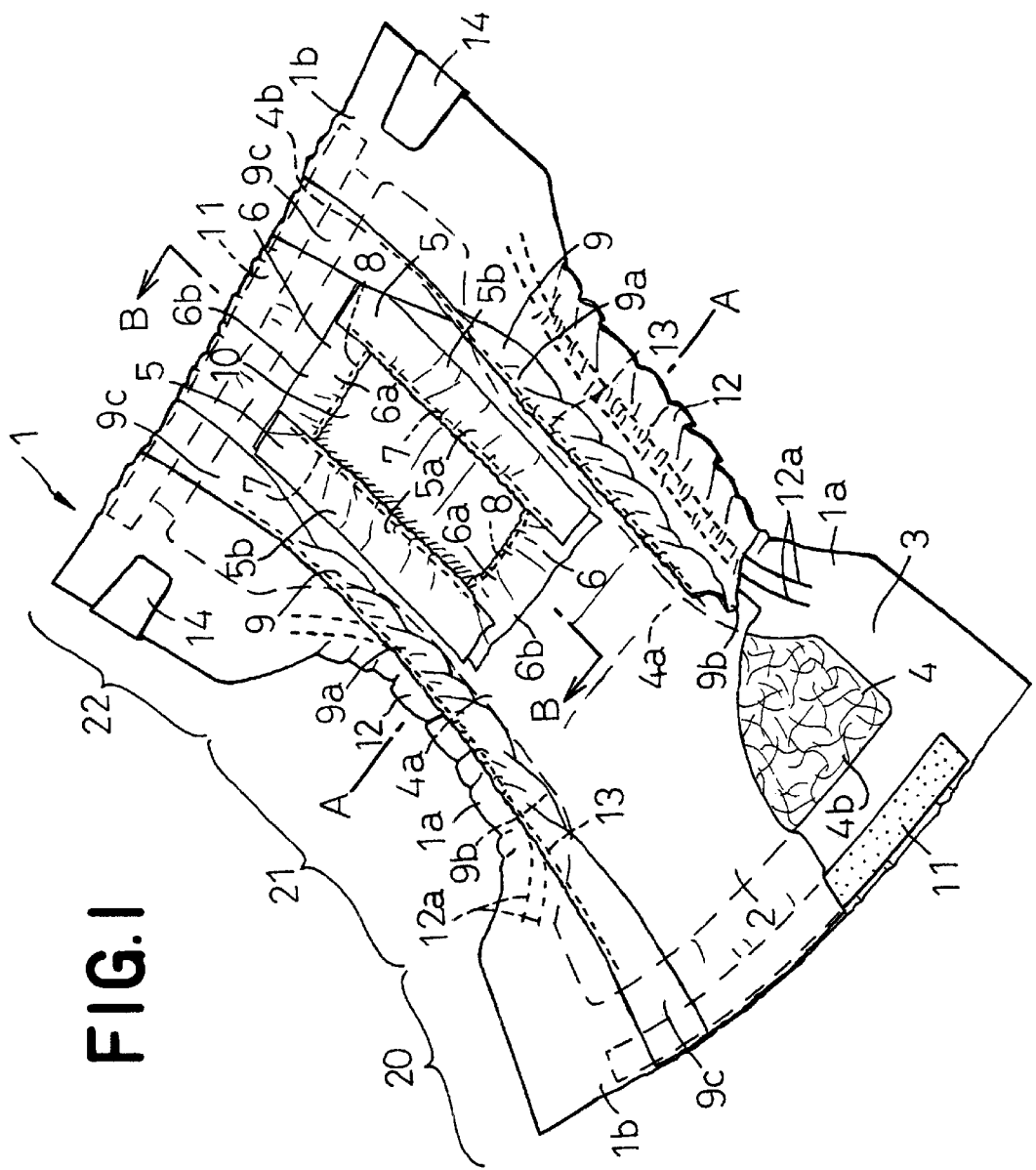
FIG. 1 is a partially cutaway perspective view showing a disposable diaper realized in accordance with one embodiment of this invention.

FIG. 1 is a partially cutaway perspective view showing a diaper formed by a laminated panel 1. The panel 1 comprises a liquid-pervious topsheet 2, a liquid-impervious backsheet 3 and a liquid-absorbent core 4 disposed between the topsheet 2 and the backsheet 3 and joined to the inner surface of at least one of the topsheet 2 and the backsheets 3. The panel 1 has a front waist region 20, a rear waist region 22 and a crotch region 21 extending between the front and rear waist regions 20, 22. The panel 1 is contoured by transversely opposite side edges 1a longitudinally extending and curved inwardly of the panel 1 in the crotch region 21 and longitudinally opposite ends 1b extending transversely of the panel 1.

The panel 1 further includes a feces receiving section 10 three-dimensionally defined by a pair of first barrier flaps 5 transversely opposed to and spaced from each other over the upper surface of the panel 1 and respectively extending longitudinally between the crotch region 21 and the rear waist region 22 and a pair of second barrier flaps 6 lying on the crotch region 21 and the rear waist region 22, respectively so as to extend transversely between the pair of first barrier flaps 5. The feces receiving section 10 extends from a substantially central zone of the crotch region 21 to a zone adjacent the longitudinal end 1b of the rear waist region 22. Each of the first barrier flaps 5 is provided on its free side edge 5a extending transversely inward from its proximal side edge 5b with a longitudinally extending elastic member 7 secured under tension to the free side edge 5a. Each of the second barrier flaps 6 is provided on its free side edge 6a extending longitudinally inward from its proximal side edge 6b with a transversely extending elastic member 8 secured under tension to the free side edge 8b.

The panel 1 still further includes a pair of barrier cuffs 9 lying between the transversely opposite side edges 1a of the panel 1 and the first barrier flaps 5 and longitudinally extending immediately outside transversely opposite side edges 4a, respectively. Each of the barrier cuffs 9 comprises a free side edge 9a fixed neither to the topsheet 2 nor to the backsheet 3 in the crotch region 21, a longitudinally extending proximal side edge 9b and longitudinally opposite ends 9c lying on the front and rear waist regions 20, 22, respectively. The free side edge 9a of the barrier cuff 9 extending transversely outward from the proximal side edge 9b as well as the longitudinally opposite ends 9c have their contours coinciding with the contour defined by each of the transversely opposite side edges of the backsheet 3.

Each of the barrier cuffs 9 has its proximal side edge 9b lying immediately outside the associated side edge 4a of the core 4 and joined to the upper surface of the topsheet 2 and its longitudinally opposite ends 9c collapsed outwardly of the panel 1 and joined to the upper surface of the topsheet 2. The barrier cuff 9 is provided along its free side edge 9a with a longitudinally extending elastic member 13 secured under tension thereto. The panel 1 is illustrated as longitudinally curved with its inner surface lying inside and the barrier cuffs 9 are illustrated as rising on the panel 1 under contraction of the respective elastic members 13.

The panel 1 also includes a pair of gasket cuffs 12 lying between the transversely opposite side edges 1a and the proximal side edges 9b of the barrier cuffs 9. The gasket cuffs 12 are formed with portions of the backsheet 3 extending outward from transversely opposite side edges of the core 4 and outer extensions of the barrier cuffs 9 lying between the proximal side edges 9b of the barrier cuffs 9 and the transversely opposite side edges 1a of the panel 1. The gasket cuffs 12 are provided with elastic members 12a extending longitudinally of the gasket cuff 12 and intended to be associated with leg-openings. The elastic members 12a are disposed between the topsheet 2 and the backsheet 3 and secured under tension to at least one of these two sheets 2, 3. The longitudinally opposite ends 1b of the panel 1 are also provided with elastic members 11 extending transversely of the panel 1 and intended to be associated with a waist-opening. These elastic members 11 are disposed between the backsheet 3 and the respective barrier cuffs 9 and secured under tension to at least one of the backsheet 3 and the barrier cuffs 9. In the rear waist region 22 of the panel 1, tape fasteners 14 extend transversely inward from the transversely opposite side edges 1a of the panel 1.

Figure 2:
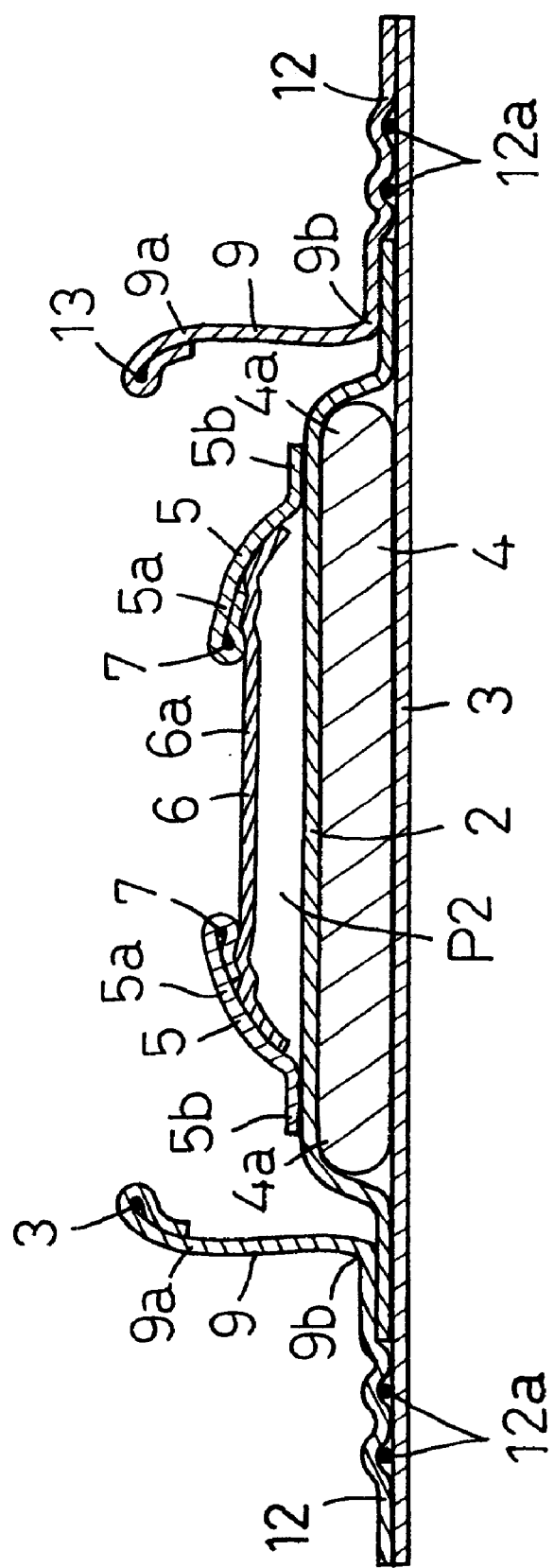
FIG. 2 is a fragmentary sectional view taken along line A—A in FIG. 1.
Figure 3:
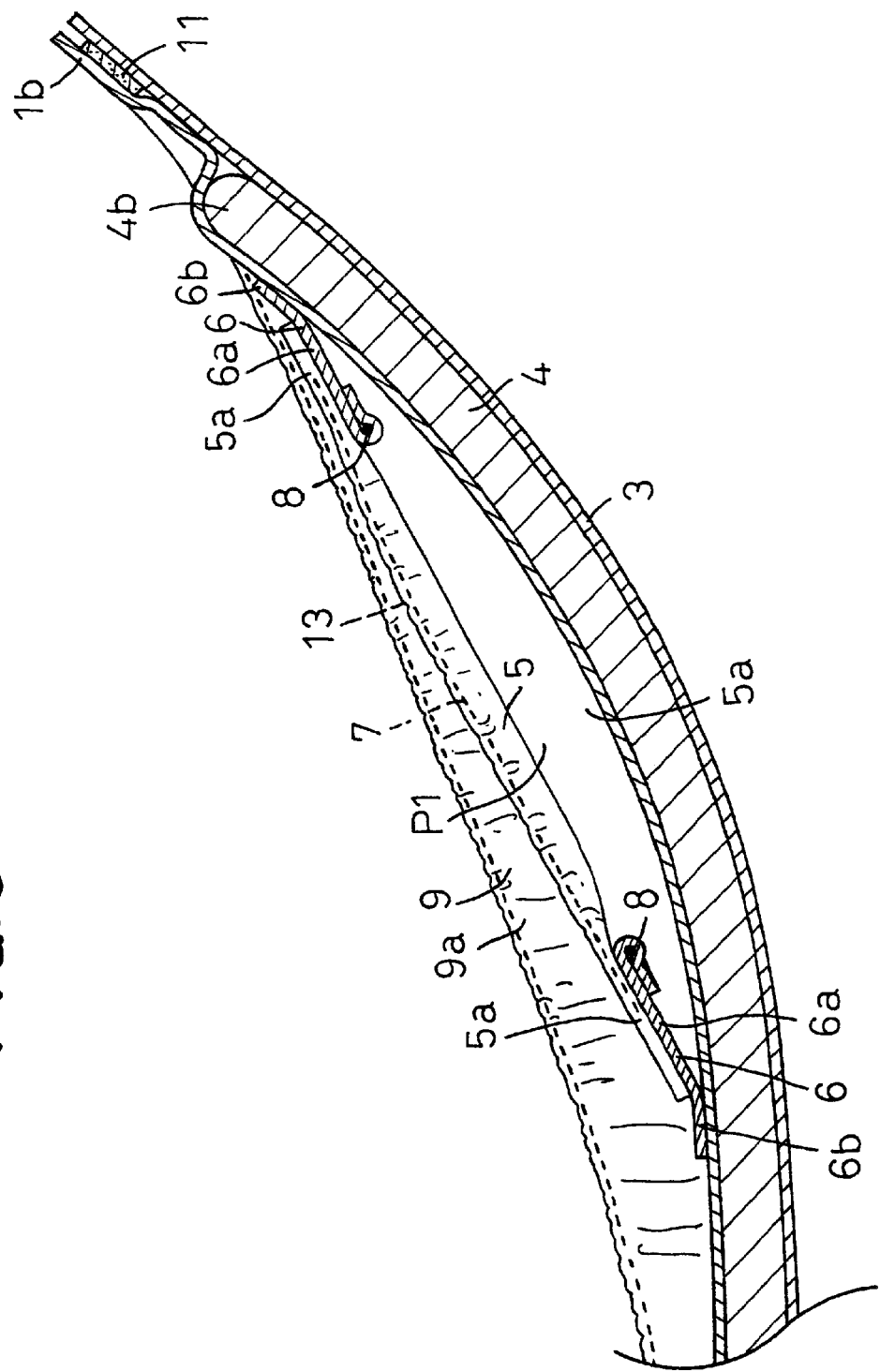
FIG. 3 is a fragmentary sectional view taken along line B—B in FIG. 1.

In the front waist region 20, the panel 1 is provided on its outer surface with pieces of target tape on which respective the tape fasteners 14 are anchored. The tape fasteners 14 may be anchored on the pieces of target tape by means of adhesive agent applied on inner surfaces of the tape fasteners 14 to form the waist-opening and a pair of the leg-openings (not shown) FIGS. 2 and 3 are fragmentary sectional views taken along line A—A and a line B—B, respectively, in FIG. 1. Each of the first barrier flap 5 has its proximal side edge 5b extending longitudinally of the panel 1 lying inside the associated one of the transversely opposite side edges 4a of the core 4 and fixed to the upper surface of the topsheet 2 by means of adhesive agent (not shown). In the crotch region 21, each of the second barrier flap 6 has its proximal side section 6b extending transversely of the panel 1 and fixed to the upper surface of the topsheet 2 by means of adhesive agent (not shown). In the rear waist region 22, the fixed side edge 6b extending transversely of the panel 1 lies inside the associated one of longitudinally opposite ends and is fixed to the upper surface of the topsheet 2 by means of adhesive agent (not shown).

The free side edge 5a of the first barrier flap 5 and the free side edge 6a of the second barrier flap 6 are partially placed upon and joined to each other by means of adhesive agent (not shown) with the first barrier flap 5 overlying the second barrier flap 6. The free side edges 5a, 6a of the first and second barrier flaps 5, 6 are folded inwardly of the panel 1 to wrap the elastic members 7, 8 with these free side edges 5a, 6a.

The first barrier flap 5 cooperates with the topsheet 2 to form a pocket P1 opening inward transversely of the panel 1 while the second barrier flap 6 cooperates with the topsheet 2 to form a pocket P2 opening inward longitudinally of the panel 1.

In the panel 1, the topsheet 2 extends slightly beyond the transversely opposite side edges 4a of the core 4 and the backsheet 3 extends transversely outward beyond the outer side edges of the topsheet 2. These extensions of the backsheet 3 beyond the outer side edges of the topsheet 2 are joined to the portions of the respective barrier cuffs 9 transversely outward from their proximal side edges 9b. The free side edge 9a of the respective barrier cuffs 9 are collapsed inwardly of the panel 1 so as to wrap the elastic members 13, respectively.

The proximal side edges 5b of the respective first upper sheets 5 are joined to the topsheet 2 along zones extending inside the transversely opposite edges 4a of the core 4 so that the transversely opposite edges 4a of the core defined between the barrier cuffs 9 and the first barrier flaps 5 can reliably absorb an amount of discharged urine possibly flowing into these spaces.

In the rear waist region 22 of the panel 1, the proximal side edges 6b of the respective second barrier flaps 6 are joined to the topsheet 2 along zones extending inside the longitudinally opposite ends 4b of the core 4 so that the longitudinally opposite ends 4b of the core 4 can reliably absorb an amount of discharged urine possibly flowing into these spaces.

Figure 4:
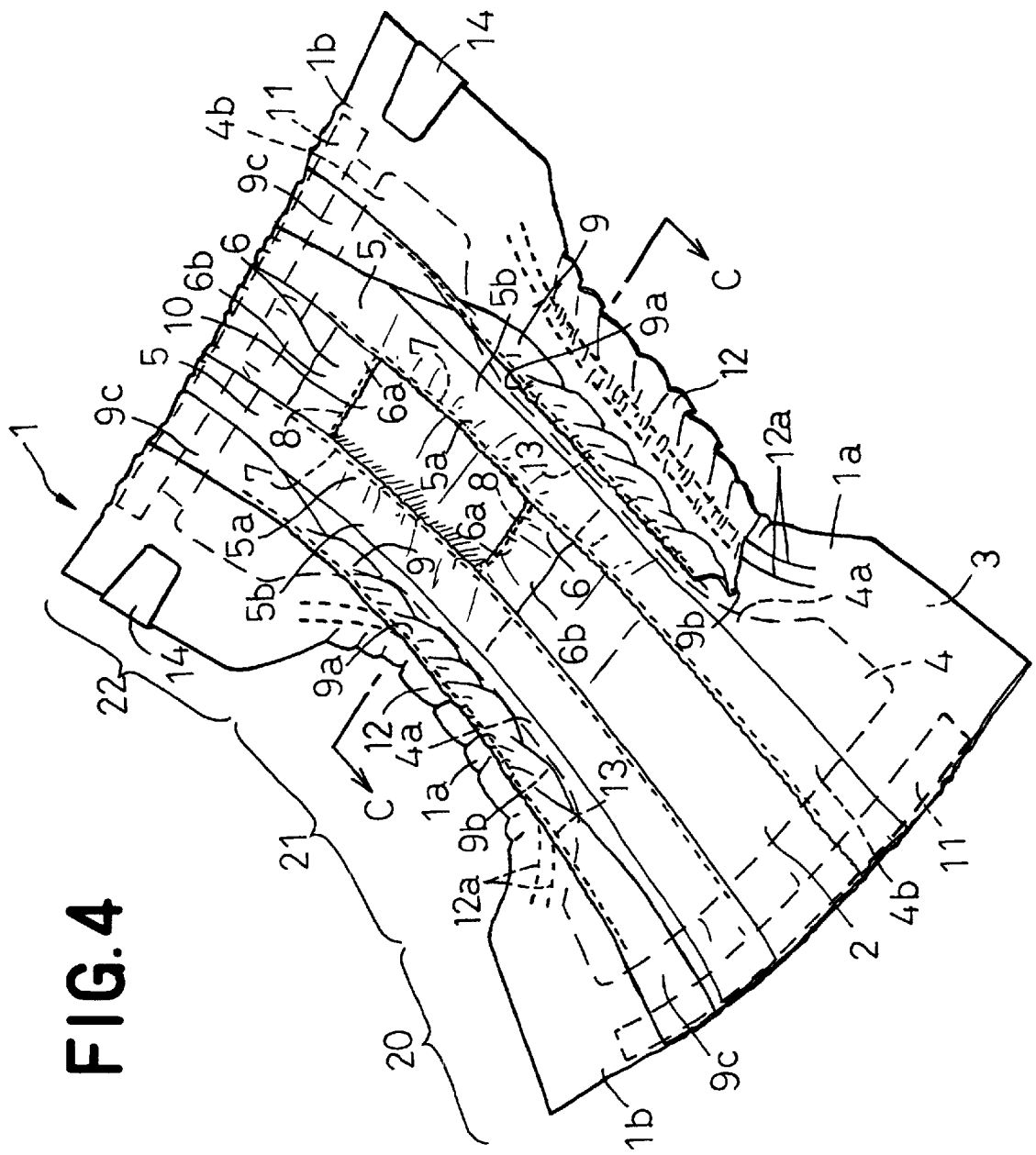
FIG. 4 is a view similar to FIG. 1 but showing a disposable diaper realized in a manner different from the manner in which the diaper of FIG. 1 is realized.
Figure 5:
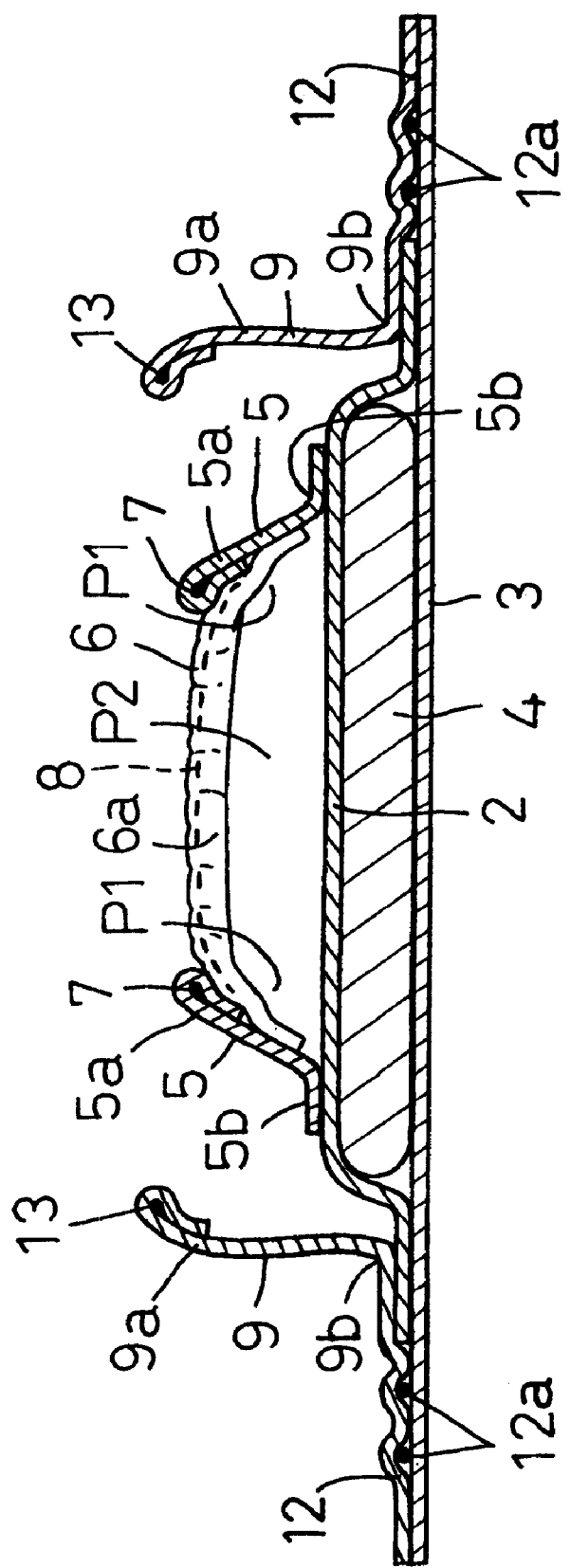
FIG. 5 is a fragmentary sectional view taken along line C—C in FIG. 4.

FIG. 4 is a perspective view showing a panel 1 realized in a manner different from the manner in which the panel 1 of FIG. 1 is realized as partially broken away and FIG. 5 is a fragmentary sectional view taken along line C—C in FIG. 4. The panel 1 according to this alternative embodiment is similar to the panel 1 of FIG. 1 in that the panel 1 comprising the topsheet 2 and the backsheet 3 and the core 4 disposed between them has the feces receiving section 10 extending from the substantially middle zone of the crotch region 21 to the vicinity of the longitudinal end 1b of the rear waist region 22, and the pair of barrier cuffs 9 extending longitudinally of the panel 1.

The first barrier flaps 5 are transversely opposite and spaced from each other over the upper surface of the panel 1 and extending between the longitudinally opposite ends 1b of the panel 1. Each of the first barrier flaps 5 has its longitudinally opposite ends 5c lying on the longitudinally opposite ends 1b of the panel 1, collapsed inwardly of the panel 1 and joined to the topsheet 2 in such collapsed state. The free side section 5a of the first barrier flaps 5 extending transversely inward from its proximal side section 5b is provided with the longitudinally extending elastic member 7 secured under tension thereto. The second barrier flaps 6 lie in the crotch region 21 and the rear waist region 22, respectively, and transversely extend between the pair of first barrier flaps 5. The free side section 6a of the second barrier flap 6 extending longitudinally inward from its proximal side edge 6b is provided with the transversely extending elastic member 8 secured under tension thereto. The free side edge 5a of the first upper sheet 5 and the free side section 6a of the second barrier flap 6 are partially placed upon and joined to each other with the first barrier flaps 5 overlying the second barrier flap 6.

The panel 1 of FIG. 4 differs from the panel 1 of FIG. 1 in that the elastic members 7 extend fully between the longitudinally opposite ends 1b of the panel 1. These elastic members 7 contract fully between the longitudinally opposite ends 1b of the panel 1 as the panel 1 is longitudinally curved with its inner surface inside. Accordingly, such an arrangement of the elastic members 7 causes the free side edge 5a of the respective first barrier flaps 5 to rise on the panel 1 more reliably than in the case of the panel 1 illustrated by FIG. 1. The proximal side edges 6b of the second barrier flaps 6 are lifted above the panel 1 by the free side edges 5a of the first barrier flaps 5 rising on the panel 1. Rising of the first and second barrier flaps 5, 6 open the pockets P1, P2 sufficiently to receive a large amount of excretion in these pockets P1, P2.

The topsheet 2 is made of a liquid-pervious, preferably liquid-pervious but hydrophobic sheet such as a nonwoven fabric or porous plastic film. The backsheet 3 is formed by a liquid-impervious plastic film or a laminated sheet of plastic film and hydrophobic nonwoven fabric, preferably a breathable but liquid-impervious sheet.

The barrier cuffs 9 as well as the first and second barrier flaps 5, 6 are made of a breathable but liquid-impervious nonwoven fabric or breathable but liquid-impervious elastic nonwoven fabric. In the case of the barrier cuffs 9 made of elastic nonwoven fabric, the barrier cuffs 9 may be joined under tension to the panel 1. In the case of the first and second barrier flaps 5, 6 made of elastic nonwoven fabric, the barrier flaps 5, 6 may be bonded to the panel 1 with the first barrier flaps 5 being tensioned longitudinally while the second barrier flaps 6 being tensioned transversely of the panel 1. Use of elastic nonwoven fabric as the stock materials for the barrier cuffs 9, the first barrier flaps 5 and the second barrier flaps 6 can eliminate it to provide the free side edges 9a of the barrier cuffs 9, the free side edges 5a of the first barrier flaps 5 and the free side edges 6a of the second barrier flaps 6 with the elastic members 7, 8, 13, respectively.

Nonwoven fabric useful for this invention may be selected from a group including types of spun lace, needle punch, melt blown, thermal bond, spun bond and chemical bond. A suitable basis weight of nonwoven fabric is 15~80 g/m$^2$, preferably 20~60 g/m$^2$. A component fiber of nonwoven fabric may be selected from a group including polyolefine, polyester and polyamide fibers and polyethylene/polypropylene or polyester conjugated fiber.

The core 4 is a mixture of fluff pulp and polymer particles of high water absorptivity compressed to a desired thickness and entirely covered with a water-pervious sheet such as tissue paper. Joining of the sheets and attaching of the elastic members may be carried out using a known adhesive agent such as hot melt adhesive agent, and glue and a known heat-sealing technique.

The disposable diaper according to this invention ensures that the excretion such as loose passage and relatively solid feces is discharged through the three-dimensional feces receiving section into the pockets formed by the first and second barrier flaps cooperating with the topsheet and then absorbed by the core through the topsheet. In this manner, it is not concerned that the excretion might flow into the front waist region or spread in the crotch region and the rear waist region. The first and second barrier flaps function to separate the excretion into urine and feces and thereby to protect a wearer from uncomfortable feeling otherwise given due to intermixing of urine and feces.

What is claimed is:

1. A disposable diaper having a front waist region, a rear waist region and a crotch region therebetween, said diaper comprising:

a liquid-permeable topsheet;

a liquid-impermeable backsheet;

a liquid-absorbent core disposed between the liquid-permeable topsheet and the liquid-impermeable backsheet;

a pair of elasticized barrier cuffs longitudinally extending outward from laterally opposite side edges of said liquid-absorbent core;

a pair of elasticized gasket cuffs longitudinally extending adjacent said gasket cuffs on an upper surface of said diaper; and a feces receiving section extending at least partially across said crotch and said rear waist regions between the pair of barrier cuffs, said feces receiving section being defined by a pair of elasticized first barrier flaps that are transversely opposed to and spaced apart from each other and extend longitudinally of said diaper, and a pair of elasticized second barrier flaps that are longitudinally opposed to and spaced apart from each other and extend transversely between said pair of first barrier flaps and connect to said pair of first barrier flaps.

2. The diaper according to claim 1, wherein longitudinally opposite ends of said pair of first barrier flaps are joined to the upper surface of said diaper so as to be collapsed inward transversely of said diaper.

3. The diaper according to claim 1, wherein proximal side edges of said pair of first barrier flaps lie inside the transversely opposite side edges of said liquid-absorbent core.

* * * * *